United States Patent [19]

Priddy

[11] 4,178,263

[45] Dec. 11, 1979

[54] ORGANIC PEROXIDE COMPOSITIONS

[75] Inventor: Duane B. Priddy, Coleman, Mich.

[73] Assignee: The Dow Chemical Company, Midland, Mich.

[21] Appl. No.: 846,746

[22] Filed: Oct. 31, 1977

Related U.S. Application Data

[62] Division of Ser. No. 758,282, Jan. 10, 1977, abandoned.

[51] Int. Cl.$^2$ .................... C11D 3/39; C07C 179/06
[52] U.S. Cl. ............................ 252/186; 8/111; 252/95; 252/99; 423/272
[58] Field of Search ............ 252/186, 95, 99; 8/111; 260/502 R, 610 A; 423/272, 273

[56] References Cited

U.S. PATENT DOCUMENTS

| | | | |
|---|---|---|---|
| 3,462,370 | 8/1969 | Winter et al. | 252/186 |
| 3,575,918 | 4/1971 | Daniels et al. | 252/186 |
| 3,649,548 | 3/1972 | McCloskey et al. | 252/186 |
| 3,867,461 | 2/1975 | Leveskis | 252/186 |

*Primary Examiner*—Benjamin R. Padgett
*Assistant Examiner*—Irwin Gluck
*Attorney, Agent, or Firm*—R. B. Ingraham

[57] ABSTRACT

Organic peroxide compositions suitable for free radical polymerization, the compositions comprising a mixture of a shock-sensitive peroxide and a diluent, the diluent being a monomeric material containing olefinic unsaturation which does not readily homopolymerize.

3 Claims, No Drawings

ORGANIC PEROXIDE COMPOSITIONS

CROSS-REFERENCE TO RELATED APPLICATION

This is a division of application Ser. No. 758,282 filed Jan. 10, 1977, now abandoned.

Many organic peroxides are known and used to initiate polymerization of monomers containing olefinical unsaturation. Many such peroxides are shock-sensitive and are handled usually only in diluted form. Generally, the addition of an appropriate diluent reduces the shock-sensitivity of the organic peroxide to the point where it can be safely handled. The problem of shock-sensitivity of such peroxides has been recognized for many years, for example, U.S. Pat. No. 2,133,733 issued Oct. 18, 1938 discloses the use of liquid hydrocarbons, preferably the hydrocarbons boiling in excess of 100° in a quantity sufficient to wet the peroxide surface. U.S. Pat. No. 3,538,011 discloses the use of various plasticizers mixed with peroxides to reduce their shock-sensitivity. U.S. Pat. No. 3,557,009 discloses the use of alcohols boiling between 130° and 255° C. as a means of desensitizing peroxides. U.S. Pat. No. 3,902,596 discloses a catalyst package suitable for use in polyester systems wherein the catalyst is admixed with various oils or uncured polyester resin and the peroxy-oil composition contained within a polystyrene film envelope. Oftentimes when peroxide compositions are employed in the free-radical polymerization of olefinically unsaturated materials, the diluent material employed in the peroxide composition oftentimes has a deleterious effect on the polymer so-produced, for example, in the polymerization of polystyrenes the presence of oils, hydrocarbon diluents, high molecular weight hydrocarbons and the like are not readily removed from the polymer after polymerization and result in a reduction in the heat-distortion temperature. With many thermoplastic polymers, it is usually advantageous to maintain as high a heat-distortion temperature as possible, particularly when such polymers are employed for the manufacture of shaped articles such as by injection molding or thermoformed articles from extruded sheet.

It would be desirable if there were available an improved organic peroxide composition suitable for the polymerization of ethylenically unsaturated monomers.

It would also be desirable if there were available an improved organic peroxide composition of reduced shock-sensitivity which did not significantly reduce the heat-distortion temperatures of polymers prepared therewith.

It would also be desirable if there were available organic peroxide compositions which contained as principal ingredients materials reactive in a free-radical polymerization of olefinically unsaturated monomers.

It would also be desirable if there were available an improved method for the polymerization of olefinically unsaturated monomers employing organic peroxide as a free-radical initiator.

These benefits and other advantages in accordance with the present invention are achieved in an organic peroxide composition having reduced shock-sensitivity comprising an intimate admixture of (a) a shock-sensitive organic peroxide and (b) an olefinically unsaturated monomer, the olefinically unsaturated monomer which does not homopolymerize, (a) being present in a proportion of 10 to 90 parts by weight and (b) being present in a proportion of 90 to 10 parts by weight per 100 parts by weight of (a) and (b).

Also contemplated within the scope of the present invention is an improvement in a method for polymerizing one or more olefinically unsaturated monomer, the method comprising admixing an organic peroxide with olefinically unsaturated polymerizable material maintaining the resultant mixture of monomeric material and a free-radical polymerization initiating peroxide at a polymerizing temperature and converting at least a portion of the monomeric material into polymeric material, the improvement which comprises providing the organic peroxide in admixture with a shock-desensitizing amount of an olefinically unsaturated monomer which exhibits no tendency to homopolymerize but is copolymerizable with the monomeric material.

Shock-sensitive organic peroxides which are handled in diluted form and are suitable for the practice of the present invention include: propionyl peroxide, acetyl peroxide, succinic acid peroxide, t-butyl peroxyisobutylate, cyclohexanone peroxide, methyl ethyl ketone peroxide, 2,2-bis-(t-butyl peroxy)butane, 1,1-bis(t-butyl peroxy)cyclohexane, t-butyl peroxy isopropyl carbonate, 2,5-dimethyl-2,5-bis(benzoylperoxy)hexane, t-butylperacetate, t-butylperbenzoate, and di-t-butylperoxy phthalate.

By the term "reduced shock-sensitivity" is meant reduced $E_{50}$ value as determined by Liquid Propellant Information Agency Test No. 4, Drop-Weight Test, Joint Army-Navy-Air Force Panel on Liquid Propellant Test Methods, Silver Springs, Md., March 1960.

Monomers which exhibit no tendency to homopolymerize are those monomers which in admixture with an organic polymerization inducing peroxide such as hereinbefore set forth do not polymerize to more than one percent conversion of monomer to polymer at 100 hours at 40° C. when the organic peroxide and monomer are present in a one-to-one ratio by weight. Typical non-homopolymerizing monomers include: maleic anhydride, dimethyl maleate, ethyl maleate, diethyl maleate, citriconic anhydride, dimethyl citriconate, methyl citriconate, ethyl citriconate, fumaronitrile, methyl fumurate, dimethyl fumurate, ethyl fumurate, diethyl fumurate, cinnamonitrile, methyl cinnamate, ethyl cinnamate, stilbene, and the like.

Organic peroxy initiator compositions in accordance with the present invention are useful for initiation of polymerization of a wide variety of monomers. Among the suitable ethylenically unsaturated monomers are: styrene, styrene with alkyl and halogen substituents on the ring and side chain such as o-, m- and p-methyl styrenes, alpha methyl styrene, 2,4-dimethyl styrene, 2,3-dimethyl styrene, 2,5-dimethyl styrene, alpha chlorostyrene, alpha ethyl styrene, p-ethylstyrene, m-propyl styrene, bromostyrene, dichlorostyrene, isopropenyl toluene, vinyl naphthalene, and the o-, m- and p-chlorostyrenes and bromostyrenes; esters of alpha-methylene aliphatic monocarboxylic acids, such as methyl acrylate, ethyl acrylate, n-butyl acrylate, isobutyl acrylate, dodecyl acrylate, 2-chloroethyl acrylate, 2-chloropropyl acrylate, 2,2'-dichloroisopropyl acrylate, phenyl acrylate, cyclohexyl acrylate, methyl alpha-chloroacrylate, methyl methacrylate, ethyl methacrylate, methyl ethacrylate; acrylonitrile, methacrylonitrile; vinyl esters, such as vinyl acetate, vinyl chloroacetate, vinyl propionate, vinyl butyrate, vinyl laurate, vinyl stearate, vinyl ethers such as vinyl methyl ether, vinyl isobutyl ether, vinyl 2-chloroethyl ether; vinyl ketones, such as vinyl methyl ketone, vinyl hexyl ketone, methyl isopropenyl ketone; isobutylene; vinylidene halides, such as vinylidene chloride; vinylidene chlorofluoride; N-vinyl compounds such as N-vinyl pyrrole, N-vinyl carbazole, N-vinyl indole, N-vinyl succinimide; acrolein, methacrolein, acrylamide, methacrylamide, N-methylol acrylamide; and allyl compounds such as diallyl phthalate, tetrachlorodiallyl phthalate, allyl alcohol, methallyl alcohol, allyl acetate, allyl methacrylate, diallyl carbonate, allyl lactate, allyl alphahydroxyisobutyrate, allyl trichlorosilane, allyl acrylate, diallyl malonate, diallyl oxalate, diallyl gluconate, diallyl methylgluconate, diallyl adipate, diallyl sebacate, diallyl citraconate, the diallyl ester of muconic acid, diallyl itaconate, diallyl chlorophthalate, diallyl dichlorosilane, the diallyl ester of endomethylene tetrahydrophthalic anhydride, triallyl tricarballylate, triallyl aconitate, triallyl citrate, triallyl cyanurate, triallyl phosphate, trimethallyl phosphate, tetraallyl silane, tetraallyl silicate, hexallyl disiloxane, and the like. Unsaturated olefins such as ethylene, propylene, butylene, hexene and exemplary monomers that can be employed with the initiators of this invention are 1,3-butadiene; isoprene; piperylene; 2,3-dimethyll-1,3-butadiene; 1,3-octadiene; 4,5-diethyl-1,3-octadiene; styrene; 3-methylstyrene; 3,5-diethylstyrene; 4-n-propylstyrene; 2,4,6-trimethylstyrene; 3-methyl-5-n-hexylstyrene; 2,3,4,5-tetramethylstyrene; 4-dodecylstyrene; 4-cyclohexylstyrene; 4-phenylstyrene; 4-p-tolylstyrene; 1-vinylnaphthalene; 2-vinylnaphthalene; 4-methyl-1-vinylnaphthalene; 3-ethyl-2-vinylnaphthalene; 4,5-dimethyl-1-vinylnaphthalene; 4,5-diethyl-2-vinylnaphthalene; 6-isopropyl-1-vinylnaphthalene; 2,4-diisopropyl-1-vinylnaphthalene; 4-n-propyl-5-n-butyl-2-vinylnaphthalene, and the like.

Polymerization of ethylenically unsaturated monomers employing the organic peroxy compositions in accordance with the present invention may be conducted in any of the conventional polymerization systems such as bulk, mass, mass suspension, solution, suspension and emulsion polymerization. The compositions of the present invention are readily prepared by admixing the desired peroxide with the non-homopolymerizable monomer. In cases where the monomer is liquid, such mix is readily accomplished at ambient or lower temperatures. Generally, it is desirable to add the peroxide to the monomer in the case of a liquid mixture. When the monomer is a solid at ambient temperature, generally it is desirable to pulverize the monomer to form the plurality of particles. Beneficially such particles are sufficiently small to pass a 100-mesh US sieve size screen. If it is desired that the proportion of peroxide be substantially greater than about one-to-one, the monomer should be divided into particles having maximum surface. Frequently, in order to obtain monomer of high surface, it is often desirable to dissolve the monomer in appropriate solvent and precipitate the monomer in a nonsolvent and recover the precipitate by filtering and drying.

For purposes of comparison, four samples were prepared by polymerizing styrene in a glass ampule at a temperature of 128° C. employing 0.4 parts by weight of peroxy based on the weight of the styrene. The polymerizations were carried out to about 55-65 weight percent conversion of styrene to polystyrene. The ampules and contents were then cooled. The contents were removed and devolatilized at 210° C. for a period of one hour under a pressure of three millimeters of mercury. Four initiator systems (all nonshock-sensitive in accordance with Liquid Propellant Information Agency, Test No. 4, Drop-Weight Test) were used: one employed tertiarybutylperbenzoate admixed with silicone oil; a second was tertiarybutylperbenzoate admixed with solid maleic anhydride; the third was 1,1-bis(t-butylperoxy)cyclohexane admixed with mineral oil; and the fourth was 1,1-bis(t-butylperoxy)cyclohexane admixed with diethyl fumarate. In each case equal parts by weight of organic peroxide and diluent were employed. The devolatilized polymer was compression molded to provide a test specimen and the Vicat heat-distortion temperature of the resultant polymer determined. Employing tertiarybutylperbenzoate as the catalyst, the sample containing silicone oil had a distortion temperature of 225° F. while the sample employing maleic anhydride in place of the silicone oil had a heat-distortion temperature of 228° F. Samples employing the mineral oil and diethylfumarate had a Vicat heat-distortion temperature of 224° F. and 226° F., respectively. Although the foregoing illustrations show only the use of a single organic peroxy compound, mixture of one or more of the hereinbefore delineated organic peroxy compounds with one or more of the hereinbefore delineated non-homopolymerizable monomers are readily employed. Such mixtures are particularly beneficial where it is desired to conduct polymerization over an extended range of temperatures.

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth and defined in the hereto-appended claims.

What is claimed is:

1. An organic peroxide composition having reduced shock-sensitivity, the composition being consisting essentially of (a) a shock-sensitive organic peroxide and (b) an olefinically unsaturated monomer, the olefinically unsaturated monomer which does not homopolymerize, (a) being present in a proportion of 10 to 90 parts of weight and (b) being present in a proportion of 90 to 10 parts by weight per 100 parts by weight of (a) plus (b).

2. The peroxide composition of claim 1 wherein the olefinically unsaturated monomer at ambient temperature is particulate.

3. The peroxide composition of claim 2 wherein the particles of the particulate monomer are sufficiently small to pass a 100-mesh US sieve size screen.

* * * * *